United States Patent [19]
Lewenstam et al.

[11] Patent Number: 5,498,323
[45] Date of Patent: Mar. 12, 1996

[54] PROCEDURE AND APPARATUS FOR THE DETERMINATION OF CONCENTRATION OF AMMONIA, AND A PROCEDURE FOR THE MANUFACTURING OF A DETECTOR

[75] Inventors: Andrzej Lewenstam, Helsinki, Finland; Wojciech Matuszewski; Marek Trojanowicz, both of Varsova, Poland

[73] Assignee: Kone Oy, Helsinki, Finland

[21] Appl. No.: 193,396

[22] Filed: Feb. 7, 1994

[30] Foreign Application Priority Data

Mar. 3, 1993 [FI] Finland ................................. 930955

[51] Int. Cl.⁶ .................................................. G01N 27/26
[52] U.S. Cl. ...................... 205/780.5; 204/412; 204/418; 204/431; 205/792
[58] Field of Search ........................... 204/153.14, 412, 204/416, 418, 431, 432

[56] References Cited

U.S. PATENT DOCUMENTS

| | | | |
|---|---|---|---|
| 4,235,689 | 11/1980 | Petersen et al. | 204/153.14 |
| 4,681,115 | 7/1987 | Holscher | 204/415 |
| 4,968,400 | 11/1990 | Shimomura et al. | 204/403 |
| 5,089,294 | 2/1992 | Ratcliffe | 427/108 |
| 5,198,092 | 3/1993 | Kiesele et al. | 204/153.14 |

OTHER PUBLICATIONS

Dall'Olio et al., Akad. Sci., Ser. C. 267 (1968)*8, pp. 433–435.
Miasik et al, Conducting Polymers, Alcacer (ed.), D. Reidel Publishing Company (1987)*, pp. 189–197.
Kanazawa et al, J. C. S. Chem. Comm (1979)*, pp. 854–855.
Bull et al, J. Electrochem. Soc., 129 (1982), pp. 1009–1015.
Diaz et al, J. C. S. Chem. Comm. (1979), pp. 635–636.

*Primary Examiner*—T. Tung
*Attorney, Agent, or Firm*—Birch, Stewart, Kolasch & Birch

[57] ABSTRACT

A procedure and an apparatus to determine the concentration of dissolved ammonia. A polypyrrole electrode (2), a reference electrode (1) and an auxiliary electrode (5) are placed in the liquid to be analyzed and the concentration of ammonia dissolved in the liquid is determined by a potential applied between the polypyrrole electrode (2) and the reference electrode (1) and of the current flowing between the polypyrrole electrode (2) and the auxiliary electrode (5). A polypyrrole layer (4) is formed on a platinum substrate (3).

5 Claims, 1 Drawing Sheet

PROCEDURE AND APPARATUS FOR THE DETERMINATION OF CONCENTRATION OF AMMONIA, AND A PROCEDURE FOR THE MANUFACTURING OF A DETECTOR

FIELD OF THE INVENTION

The present invention relates to a procedure and an apparatus for the determination of concentration of ammonia. In addition, the invention relates to a procedure for manufacturing a detector and to the use of a detector for the determination of ammonia.

DESCRIPTION OF THE BACKGROUND ART

In the prior art, various methods and devices are used for the determination of concentration of ammonia in chemical and biochemical compounds. However, there is no previously known procedure or apparatus that enables the ammonia content of a liquid to be quickly determined without complex analyses.

Dall'Olio et al, Akad. Sci., Ser.C 267 (1968) 8, p.433–435 disclosed the possibility of electrochemical polymerisation of pyrrole. Diaz et al, J.C.S. Chem. Comm. (1979) p.635–636 disclosed the conditions that allow electrochemical polymerisation of pyrrole on platinum, resulting in a durable electrode film with enhanced electrical conductivity and strong adherence. Bull et al, J. Electrochem. Soc., 129 (1982), showed that a polypyrrole film deposited on platinum exhibits electron transfer reactions in solutions. Kanazawa et al, J.C.S.Chem. Comm. (1979), p.855–856, disclosed that exposing a polypyrrole film to ammonia reduces the conductivity of the film. Miasik et al, Conducting Polymers, Alcacer (ed.), D. Reidel Publishing Company (1987), p. 189–197, disclosed that a thin polypyrrole film formed by electropolymerization from an aqueous solution of pyrrole monomer and $LiBF_4$ can be used as a chemiresistor sensitive to ammonia, i.e. as a resistor whose resistance value depends on the chemical composition of the substance which surrounds it and is in contact with it, in this case ammonia. The film was able to detect an ammonia content of 0.1% in air. U.S. Pat. No. 5,089,294 disclosed that a chemiresistor based on polypyrrole film can be used for detecting the concentration of ammonia in atmospheric air by measuring the change in the resistance value.

SUMMARY OF THE INVENTION

The object of the present invention is to achieve a new method and a new apparatus for the determination of ammonia dissolved in a liquid, as well as a new method for the manufacturing of a polypyrrole-based ammonia detector.

The present invention is based on the discovery that a highly sensitive ammonia detector can be produced by coating a chemically inert, electrically conducting substrate with a film of polypyrrole. By applying an electric potential to an instrument containing such a detector and by measuring the electric current when the polypyrrole film is in contact with the solution under study, amperometric determination of the ammonia content of the liquid is achieved by reason of the proportionality between the current and the concentration of ammonia.

The invention provides several advantages. For example an analysis signal that is directly proportional to the concentration of ammonia in the substance, high selectivity due to electrochemically induced properties of the detecting element, good sensitivity and reproducibility of the signal, long service life and easy regeneration of the detecting layer, possibility of miniaturization and mechanical working of the detector can be achieved.

Other objects and further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

In the following, the invention is described in detail by the aid of its preferred embodiments. In addition to the examples, reference is made to the drawings which are given by way of illustration only, and thus are not limitative of the present invention, and in which.

DETAILED DESCRIPTION OF THE PREFERRED EMBODIMENTS

Figure 1:
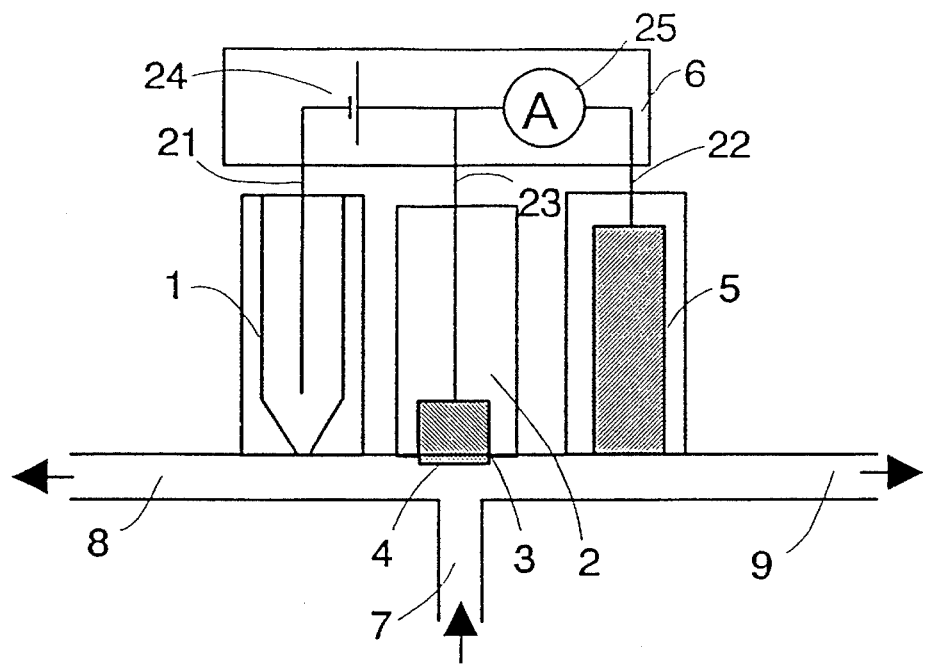
FIG. 1 presents a measuring arrangement according to the invention.

A detector sensitive to ammonia is obtained by immersing a conductive substrate in water containing dissolved pyrrole monomer and a suitable ion doping and by electropolymerizing the pyrrole in this solution to form a conductive polypyrrole film. More specifically, an amperometric ammonia detector can be produced in an aqueous or a non-aqueous solution containing dissolved pyrrole monomer and a saline ion doping in appropriate concentrations. The conducting substrate (electrode) is then coated by immersing it in the above-mentioned solution and connecting it to a controlled source of electric current or voltage, and/or by varying the voltage or current cyclically as a function of time. In this way, a conducting polymer (here polypyrrole) film of the required thickness is formed on the substrate. However, according to the present invention, a thickness of 0.4 to 30 µm is optimal. The coated substrate is then washed with water and stored in a slightly alkaline buffer solution.

For the measurements of ammonia, a selected constant voltage is applied between the coated (polypyrrole) electrode and a reference electrode (e.g. a silver chloride electrode). The resulting current that flows between the coated electrode and the auxiliary electrode indicates the concentration of ammonia in the solution. The electric current is directly proportional to the concentration of ammonia within a certain range of concentration values of the ammonia solution. This current is in fact the current of ammonia-dependent electrolysis at the detector surface and is known in electrochemistry as Faraday current. Its magnitude is not dependent on the electric resistance of the active element of the detector, which is what distinguishes this amperometric method of measurement from all methods based on the measurement of the resistance of the active element.

EXAMPLE 1

A platinum disk of diameter 1.5 mm is placed in a glass tube and polished with diamond paste 7 µm and then with aluminium oxide pastes 1 and 0.3 µm. The disk is then washed in deionized water and methanol and dried at room temperature. Freshly distilled pyrrole (6.4 g/liter) deoxygenated with argon (for 15 min.) and pure sodium chloride (5.8 g/liter) are dissolved in distilled water deoxgenated with argon in order to obtain a 0.1 mol/liter concentration of these substances.

The platinum disk is coated by electropolymerization in 40 ml of the above-described solution by applying a voltage of +0.8 V to a silver chloride electrode for 3 min., using a carbon rod of diameter 5 mm as an auxiliary electrode. During the electropolymerization, the solution is stirred with a magnetic agitator. After 3 min. of electropolymerization, the film-coated electrode is washed with distilled water and immersed in a borate buffer solution having a concentration of 0.05 mol/liter and a pH of 9.2.

The electrode thus produced is then used for the measurement of dissolved ammonia. The electrode is polarized to +0.3 V against a silver chloride electrode and the current is drained through a platinum auxiliary electrode of diameter 1.5 mm. The ammonia detector works together with the reference and auxiliary electrodes in a typical three-electrode system.

The electrodes can be placed in any cell system such as a beaker or a flow-through cell, the working principle of which is illustrated by FIG. 1. The solution to be analyzed is passed in through the intake 7 of the flow-through cell and passed out through the exit tubes 8 and 9 branching out from the intake tube 7. Placed at the branching point of the tubes is a polypyrrole-coated detector as provided by the invention. The detector consists of a polypyrrole layer 4, which is in contact with the solution, and a substrate 3 on which said layer 4 has been deposited and which consists of an inert conducting material such as gold, silver, platinum or an equivalent. The polypyrrole electrode 2 containing the detector is connected via a conductor 23 to a measuring unit 6 containing a voltage source 24 and an ammeter 25. Placed at a distance from electrode 2 in the flow tube are also a reference electrode 1 and an auxiliary electrode 5, both of which are in contact with the liquid under measurement. The reference electrode is connected by conductor 21 to the measuring unit 6 and further via the voltage source 24 and/or ammeter to the polypyrrole electrode 2. A preferable voltage level is 0.2–1.0 V. Similarly, the auxiliary electrode 5 is connected by conductor 22 via the ammeter 25 in the measuring unit to the polypyrrole electrode 2. Alternatively, a constant current source is connected to the polypyrrole electrode 2 and to the auxiliary electrode 5 and the measurement of voltage is made between the reference electrode 1 and the polypyrrole electrode 2.

The current flowing through the two electrodes, i.e. through the coated electrode and the auxiliary electrode, is a linear function of the concentration of dissolved ammonia in the range 0.001 to 1 mmol of ammonia per liter. The service life of the ammonia detector described is 20000 samples.

EXAMPLE 2

Figure 2:
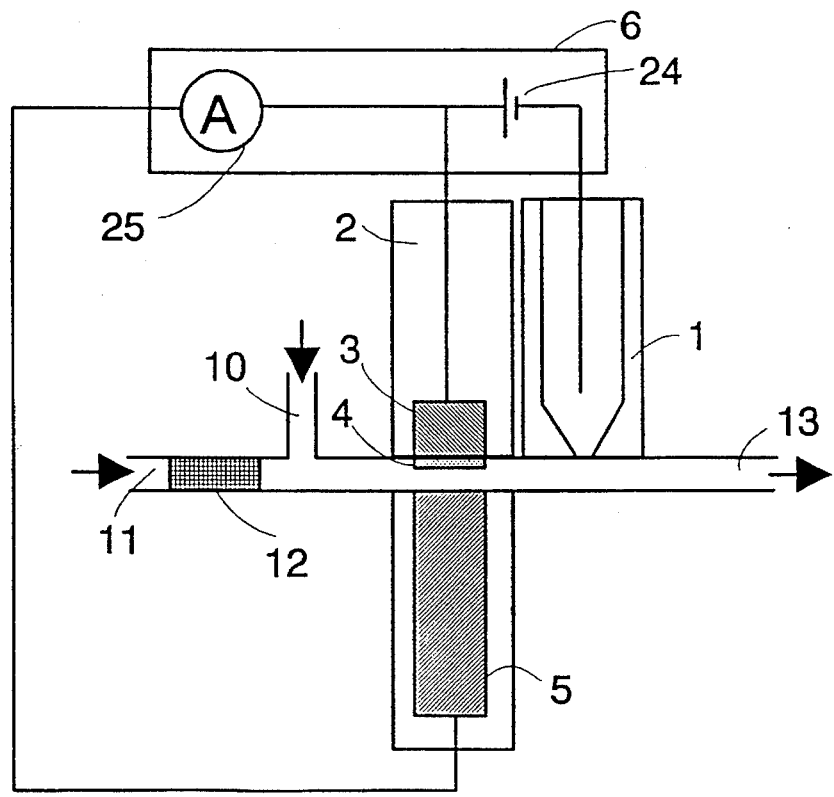
FIG. 2 presents another measuring arrangement according to the invention.

In this example, the measurement system of the invention is used for the measurement of the ammonia produced in the enzymatic decomposition of urea. For this purpose, the flow-through cell is modified so as to allow a solution containing urea to come into contact with urease at pH 7.4 and the pH to be changed to 9.2 before measurement of the ammonia released from enzymatically decomposed urea. As illustrated by FIG. 2, the solution to be measured is taken in through the inlet tube 11 of the cell and passed through an enzyme column 12. A buffer solution is brought in through inlet 10 and allowed to mix with the solution under study. The solution thus formed is passed on between a polypyrrole electrode 2 provided with a film of polypyrrole and an auxiliary electrode 5 made e.g. of platinum. The solution is passed into an exit tube 13 past a (silver chloride) reference electrode 1. The polypyrrole electrode 2 is connected to the reference electrode 1 with a potential difference between them, and an ammeter is connected between the polypyrrole electrode 2 and the auxiliary electrode 5 to measure the current flowing through these electrodes.

A linear dependence between the measured current and the concentration of urea is observed in the concentration range of 0.005 to 50 mmol/liter of urea.

In the above, the invention has been described by the aid of some of its preferred embodiments. However, it is obvious to a person skilled in the art that the invention is not confined solely to the examples presented above and that different embodiments of the invention may vary within the scope of the following claims.

We claim:

1. A procedure for determination of a concentration of dissolved ammonia using a three-electrode system, the procedure comprising the steps of:

placing a polypyrrole electrode, a reference electrode and an auxiliary electrode in a liquid to be analyzed;

applying a potential between the polypyrrole electrode and the reference electrode;

measuring a current flowing between the polypyrrole electrode and the auxiliary electrode as an indication of the concentration of dissolved ammonia in the liquid.

2. The procedure according to claim 1, wherein the reference electrode is a silver chloride electrode and the potential is in the range of +0.2–+1.0 volt.

3. The procedure according to claim 1, wherein the current in the step of measuring is constant and wherein the method further comprises the step of measuring the voltage between the polypyrrole electrode and the reference electrode.

4. A procedure for determination of a concentration of dissolved ammonia using a three-electrode system, the procedure comprising the steps of:

placing a polypyrrole electrode, a reference electrode and an auxiliary electrode in a liquid to be analyzed;

maintaining a constant current between the polypyrrole electrode and the auxiliary electrode;

measuring voltage between the polypyrrole electrode and the reference electrode as an indication of the concentration of dissolved ammonia in the liquid.

5. A procedure for determining presence of one of chemically and biochemically released ammonia, the procedure comprising the steps of:

placing a polypyrrole electrode, a reference electrode and an auxiliary electrode in a liquid to be analyzed;

applying a potential between the polypyrrole electrode and the reference electrode;

measuring a current flowing between the polypyrrole electrode and the auxiliary electrode as an indication of presence of ammonia in the liquid.

\* \* \* \* \*